United States Patent [19]

Saikawa et al.

[11] 4,199,566

[45] Apr. 22, 1980

[54] ANTIBACTERIAL COMPOSITION FOR MEDICAL USE

[75] Inventors: Isamu Saikawa; Takashi Yasuda; Masaru Tai; Yutaka Takashita, all of Toyama; Hiroshi Sakai, Takaoka; Michiko Mae, Toyama; Masahiro Takahata, Imizu; Susumu Mitsuhashi, Musashino, all of Japan

[73] Assignee: Toyama Chemical Company, Limited, Tokyo, Japan

[21] Appl. No.: 913,105

[22] Filed: Jun. 6, 1978

[30] Foreign Application Priority Data

Jun. 8, 1977 [JP]  Japan .................................. 52-66707

[51] Int. Cl.$^2$ ............................................. A61K 35/00
[52] U.S. Cl. .................................................... 424/114
[58] Field of Search ................................ 424/271, 114

[56] References Cited

PUBLICATIONS

Chemical Abstracts 85:33052b (1976) and Formula Index 1972–1976, p. 12419F.
The Merck Index, 8th Ed., Merck & Co., Inc., Rahway, N.J. 1968, pp. 271,354,355,674 and 771.

*Primary Examiner*—Jerome D. Goldberg
*Attorney, Agent, or Firm*—Oblon, Fisher, Spivak, McClelland & Maier

[57] ABSTRACT

An antibacterial composition for medical use comprising 6-[−)-α-(4-ethyl-2,3-dioxo-1-piperazinylcarbonylamino)phenylacetamido]penicillanic acid or a pharmaceutically acceptable salt thereof and a β-lactamase-inhibiting penicillin or cephalosporin. The composition exhibits synergistic effect which is much greater than the sum of antibacterial effects of each component used alone.

7 Claims, 3 Drawing Figures

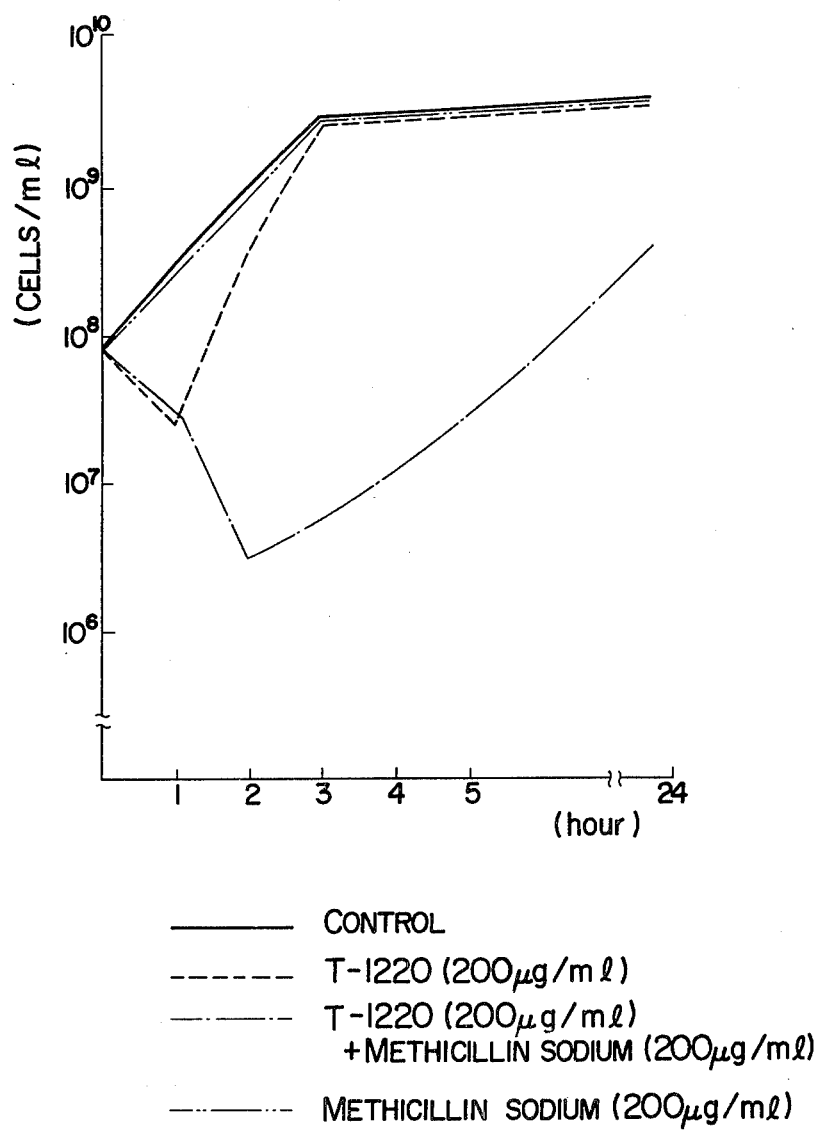

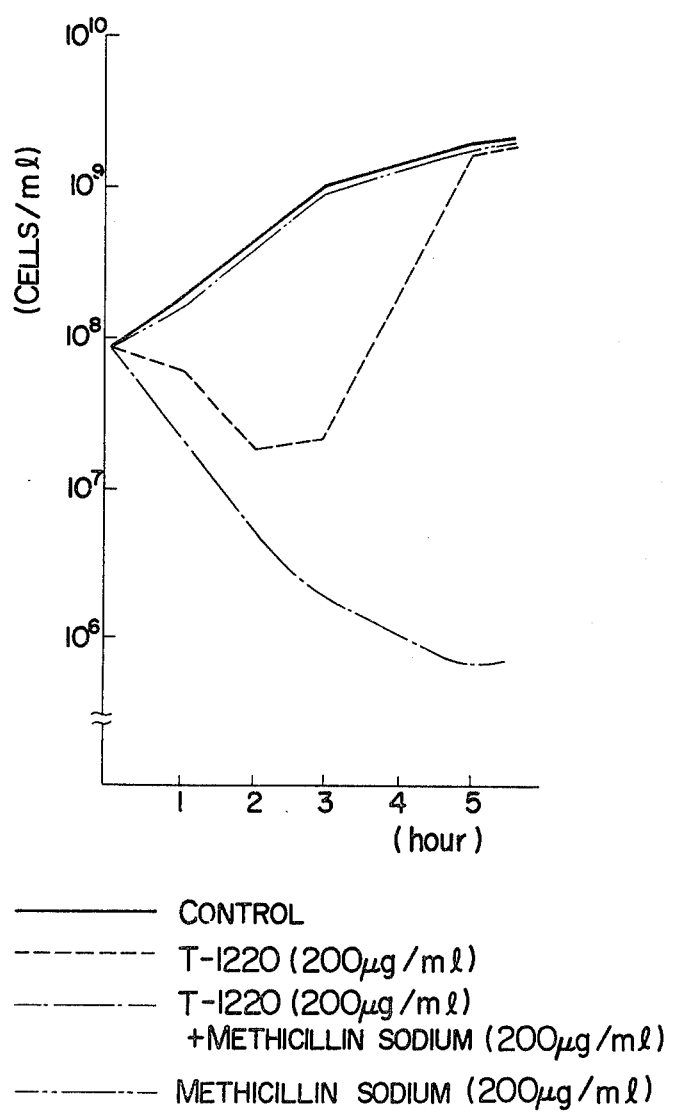

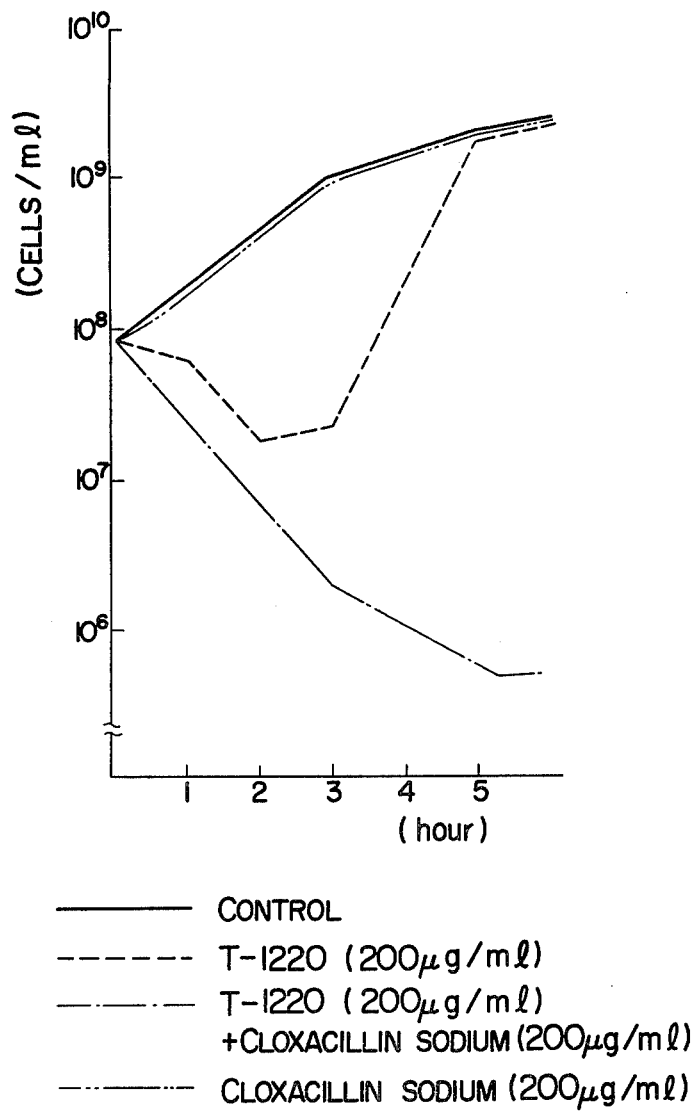

ANTIBACTERIAL COMPOSITION FOR MEDICAL USE

This invention relates to novel antibacterial compositions for medical use. More particularly, it relates to antibacterial compositions for medical use comprising 6-[D(−)-α-(4-ethyl-2,3-dioxo-1-piperazinylcarbonylamino)phenylacetamido]penicillanic acid represented by the formula [I]:

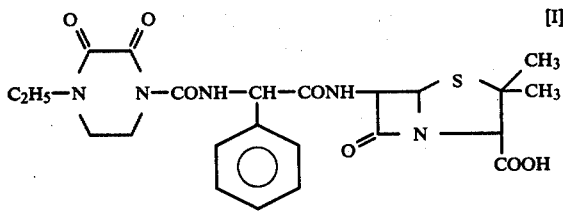

or pharmaceutically acceptable salts thereof (hereinafter said penicillanic acid and pharmaceutically acceptable salts thereof are referred to collectively as compound A) and β-lactamase-inhibiting penicillins or cephalosporins.

The compound A, which was developed by the present inventors, is a useful substance having excellent characteristics such as a broad antibacterial spectrum.

The present inventors have found as result of extensive studies that when the compound A is mixed with a β-lactamase-inhibiting penicillin or cephalosporin, the latter makes it difficult for the compound A to be affected by β-lactamase, and the resulting composition exhibits a synergistic effect on the antibacterial activity.

An object of this invention is to provide an antibacterial composition having a pronounced antibacterial activity against Gram-negative bacteria existing even in a large population, especially against *Escherichia coli*, *Proteus* species, *Klebsiella pneumoniae* and *Pseudomonas aeruginosa*.

Another object of this invention is to provide an antibacterial composition active to those pathogenic bacteria which are resistant to conventional penicillins.

A further object of this invention is to provide an antibacterial composition capable of enhancing the bactericidal speed and therapeutic effectiveness.

Other objects and advantages of this invention will become apparent from the following description.

According to this invention, there is provided an antibacterial composition for medical use comprising 6-[D(−)-α-(4-ethyl-2,3-dioxo-1-piperazinylcarbonylamino)-phenylacetamido]penicillanic acid or a pharmaceutically acceptable salt thereof and a β-lactamase-inhibiting penicillin or cephalosporin.

The above-mentioned pharmaceutically acceptable salts are those which are commonly used as penicillin salts, including salts with metals such as sodium, potassium and calcium, ammonium salt and salts with amines such as procaine, dibenzylamine, N-benzyl-β-phenethylamine, 1-ephenamine, N,N-dibenzylethylenediamine and the like.

The β-lactamase-inhibiting penicillins and cephalosporins used in this invention are, for example, Cloxacillin, Dicloxacillin, Oxacillin, Methicillin, Cefoxitin and Flucloxacillin and pharmaceutically acceptable salts thereof. These pharmaceutically acceptable salts have the same meanings as mentioned above as to salts of the compound of the formula [I].

The suitable ratio of the compound A to the β-lactamase-inhibiting penicillin or cephalosporin in the composition of this invention varies to some degrees depending on the type of target pathogenic bacteria or symptoms, but is generally in the range of from 1:0.5 to 1:1.5 (in terms of potency ratio).

In this invention, the type of β-lactamase-inhibiting penicillins or cephalosporins may be properly selected according to particular pathogenic bacteria.

The antibacterial composition for medical use according to this invention is used preferably as a parenteral injection, although it can be used in other dosage forms and through other administration routes similarly to known antibiotics such as conventional penicillins and cephalosporins. It can also be used in the form of ointment and preparation for rectal administration.

When used as an injection, the antibacterial composition of this invention can be mixed with solid or liquid carriers or diluents which are conventionally used in injections of known antibiotics. Of the carriers, sterilized water is most frequently used. The antibacterial composition of this invention may, of course, be in the form of powder which can be dissolved in suitable vehicles such as sterilized water and physiological saline solution for use as an injection.

In administering the antibacterial composition of this invention as an injection to man, intravenous injection (including instillation) or intramuscular injection is generally suitable.

The dosage of the antibacterial composition of this invention is properly selected in accordance with the ratio between the compound A and the β-lactamase-inhibiting penicillin or cephalosporin, age of the patient, and the type or symptoms of the infectious disease. The suitable dose of an injection ranges generally from 0.5 to 10 g potency per day for adults, but the dose is not limited thereto.

In administering the antibacterial composition of this invention as an injection, it can be used together with those drugs which are usually used in injections such as analgesics, for example, lidocaine hydrochloride.

The efficacy of the antibacterial composition of this invention is illustrated below with reference to Test Examples and the accompanying drawings which are diagrammatic representation of the test results. In the drawings FIG. 1 shows antibacterial activities of sodium 6-[D(−)-α-(4-ethyl-2,3-dioxo-1-piperazinylcarbonylamino)-phenylacetamido]penicillanate (referred to hereinafter as T-1220) and Methicillin sodium against *Escherichia coli* TK-3, which is clinically isolated strain, FIG. 2 shows those of T-1220 and Methicillin sodium against *Pseudomonas aeruginosa* S-12 which is clinically isolated strain, and FIG. 3 shows those of T-1220 and Cloxacillin sodium against *Pseudomonas aeruginosa* S-12 which is clinically isolated strain.

TEST EXAMPLE 1

Growth-inhibition test on clinically isolated strain

Heart Infusion agar containing a prescribed amount of Methicillin sodium or T-1220 was inoculated with the test bacterium at a rate of about $10^8$ cells/ml. After incubation for 18 hours at 37° C., the growth of the test bacterium was inspected. The results of test were as shown in Tables 1 and 2. In each table, (+) means that the test bacterium grew and (−) means that the test bacterium did not grow. From Tables 1 and 2, it is apparent that the combination of Methicillin sodium and T-1220 exhibits a synergistic effect on the inhibition of growth of the pathogenic bacteria.

Table 1.

| Methicillin sodium (μg/ml) | Escherichia coli TK-3 strain | | | | | | | |
|---|---|---|---|---|---|---|---|---|
| 3200 | − | − | − | − | + | + | + | + |
| 1600 | − | − | − | − | + | + | + | + |
| 800 | − | − | − | + | + | + | + | + |
| 400 | − | − | − | + | + | + | + | + |
| 200 | − | − | − | + | + | + | + | + |
| 100 | − | + | + | + | + | + | + | + |
| 50 | + | + | + | + | + | + | + | + |
| 0 | + | + | + | + | + | + | + | + |
|  | 3200 | 1600 | 800 | 400 | 200 | 100 | 50 | 0 |
|  |  |  | T-1220 |  |  |  |  | (μg/ml) |

Table 2.

| Methicillin sodium (μg/ml) | Pseudomonas aeruginosa S-12 strain | | | | | | | |
|---|---|---|---|---|---|---|---|---|
| 200 | − | − | − | − | + | + | + | + |
| 100 | − | − | − | − | + | + | + | + |
| 50 | − | − | − | − | + | + | + | + |
| 25 | − | − | − | − | + | + | + | + |
| 12.5 | − | + | + | + | + | + | + | + |
| 6.25 | − | + | + | + | + | + | + | + |
| 3.13 | + | + | + | + | + | + | + | + |
| 0 | + | + | + | + | + | + | + | + |
|  | 3200 | 1600 | 800 | 400 | 200 | 100 | 50 | 0 |
|  |  |  | T-1220 |  |  |  |  | (μg/ml) |

TEST EXAMPLE 2

β-Lactamase specific activity

The β-lactamase activity was assayed by the iodometric assay method at 30° C., following the procedure of Perret [C. J. Perret, "Iodometric Assay of Penicillinase," Nature, 174, 1012–1013 (1954)], except that a 0.1 molar phosphate buffer solution (pH 7.0) was used in place of the 0.2 molar phoshate buffer solution (pH 6.5). One unit of β-lactamase activity corresponds to the quantity of β-lactamase which decomposes 1 μmole/hour of T-1220 in a 0.1 molar phosphate buffer solution (pH 7.0) containing 8 m moles of the substrate.

In Table 3, there are shown β-lactamase specific activities of Escherichia coli TK-3 strain and Pseudomonas aeruginosa S-12 strain.

Table 3

| Strain | β-Lactamase activity (unit/mg dry weight) |
|---|---|
| Escherichia coli TK-3 | 329 |
| Pseudomonas aeruginosa S-12 | 63 |

TEST EXAMPLE 3

Antibacterial activity against clinically isolated strains

The following test was performed to examine whether or not the synergistic effect of the present composition confirmed by the growth inhibition test in Test Example 1 is accompanied by an antibacterial effect.

A pathogenic bacterium was inoculated at a rate of about $10^8$ cells/ml into a Heart Infusion broth containing T-1220 (200 μg/ml) alone, T-1220 (200 μg/ml) plus Methicillin sodium (200 μg/ml), T-1220 (200 μg/ml) plus Cloxacillin sodium (200 μg/ml), Methicillin sodium (200 μg/ml) alone, or Cloxacillin sodium (200 μg/ml) alone. The inoculated broth was incubated at 37° C. and the number of live cells in the culture broth was determined at predetermined time intervals.

The test results are as shown in FIGS. 1, 2 and 3, and it was confirmed that the antibacterial activity had increased by the joint use of T-1220 and Methicillin sodium or of T-1220 and Cloxacillin sodium. The minimum inhibitory concentration of T-1220, Methicillin sodium, or Cloxacillin sodium against Escherichia coli TK-3 strain or Pseudomonas aeruginosa S-12 strain was greater than 3,200 μg/ml in each case.

TEST EXAMPLE 4

Effect of combined use on experimental infection in mice

Male mice (5 mice per group) of the ICR strain, 4 weeks of age, were peritoneally inoculated with the prescribed number of pathogenic bacteria suspended in 5% mucin. After one hour and two hours following the inoculation, test preparations shown in Table 4 were subcutenously administered to examine the protection effect. The results obtained were as shown in Table 4, wherein the protection effect was expressed in terms of $ED_{50}$.

Table 4

| Infectious bacterium | Challenge dose (cells/mouse) | $ED_{50}$, mg/mouse | | |
|---|---|---|---|---|
|  |  | T-1220+ Methicillin Na (2:1) | T-1220 | Methicillin Na |
| K. pneumoniae Y-53 | $1.0 \times 10^7$ | 5.7 | >50 | >50 |
| P. aeruginosa S-111 | $1.6 \times 10^6$ | 10.2 | >50 | >50 |

As is apparent from Table 4, the synergistic effect of the combined use of T-1220 and Methicillin sodium on the inhibition of pathogenic bacteria growth, which had been found in vitro, was recognized also by the experiment of protection of animal from infection.

The test results described in the foregoing Test Examples 1 to 3 are Typical of the pharmacological activity of the antibacterial composition of this invention. When other β-lactamase-inhibiting penicillins or cephalosporins such as Oxacillin, Dicloxacillin, Cefoxitin and Flucloxacillin were used, there were obtained results similar to those obtained with Methicillin and Cloxacillin.

From the foregoing description, it is understandable that the antibacterial composition for medical use according to this invention is expected to be effective in the therapy of various diseases, the causative organisms of which are bacteria sensitive to the respective penicillins and cephalosporins. Especially, the composition of this invention will be highly useful in the therapy of various diseases including, for example, those of urinary organ which are caused by the bacteria, sensitive to the compound A, particularly belonging to Gram-negative bacteria, (Escherichia coli, Pseudomonas aeruginosa, Klebsiella Pneumoniae, Proteus species, etc.).

The present invention is illustrated below with reference to Examples which are merely illustrative and not limitative.

EXAMPLE 1

| | |
|---|---|
| Sterilized sodium 6-[D(-)-α-(4-ethyl-2, 3-dioxo-1-piperazinylcarbonylamino)-phenylacetamido]penicillanate | 500 mg potency |
| Sterilized Methicillin sodium | 500 mg potency |

The above ingredients were dissolved in 4 ml of a solution containing 0.5% (W/V) of lidocaine hydrochloride to obtain an injectable solution to be diluted when used.

EXAMPLE 2

| | |
|---|---|
| Sterilized sodium 6-[D(-)-α-(4-ethyl-2, 3-dioxo-1-piperazinylcarbonylamino)-phenylacetamido]penicillanate | 1 g potency |
| Sterilized Methicillin sodium | 500 mg potency |

The above ingredients were dissolved in 20 ml of physiological saline solution to obtain an injectable solution.

EXAMPLE 3

| | |
|---|---|
| Sterilized sodium 6-[D(-)-α-(4-ethyl-2, 3-dioxo-1-piperazinylcarbonylamino)-phenylacetamido]penicillanate | 1 g potency |
| Sterilized Methicillin sodium | 1 g potency |

The above ingredients were dissolved in 20 ml of a 5% glucose solution to obtain an injectable solution.

EXAMPLE 4

| | |
|---|---|
| Sterilized sodium 6-[D(-)-α-(4-ethyl-2, 3-dioxo-1-piperazinylcarbonylamino)-phenylacetamido]penicillanate | 2 g potency |
| Sterilized Methicillin sodium | 1 g potency |

The above ingredients were dissolved in 250 ml of a transfusion to abtain an instillation.

EXAMPLE 5

| | |
|---|---|
| Sterilized sodium 6-[D(-)-α-(4-ethyl-2, 3-dioxo-1-piperazinylcarbonylamino)-phenylacetamido]penicillanate | 250 mg potency |
| Sterilized Methicillin sodium | 250 mg potency |

The above ingredients were dissolved in 20 ml of a physiological saline solution to obtain an injectable solution.

EXAMPLE 6

| | |
|---|---|
| Sodium 6-[D-(-)-α-(4-ethyl-2, 3-dioxo-1-piperazinylcarbonylamino)-phenylacetamido]penicillanate | 1 g potency |
| Methicillin sodium | 500 mg potency |

The above ingredients were dissolved in 20 ml of distilled water and freeze-dried in a usual manner to obtain a composition. This composition was dissolved in 20 ml of physiological saline solution to obtain an injectable solution.

EXAMPLE 7

| | |
|---|---|
| Sterilized sodium 6-[D(-)-α-(4-ethyl-2, 3-dioxo-1-piperazinylcarbonylamino)-phenylacetamido]penicillanate | 1 g potency |
| Sterilized Cloxacillin sodium | 500 mg potency |

The above ingredients were dissolved in 20 ml of physiological saline solution to obtain an injectable solution.

EXAMPLE 8

| | |
|---|---|
| Sterilized sodium 6-[D(-)-α-(4-ethyl-2, 3-dioxo-1-piperazinylcarbonylamino)-phenylacetamido]penicillanate | 1 g potency |
| Sterilized Dicloxacillin sodium | 500 mg potency |

The above ingredients were dissolved in 20 ml of physiological saline solution to obtain an injectable solution.

EXAMPLE 9

| | |
|---|---|
| Sterilized sodium 6-[D(-)-α-(4-ethyl-2, 3-dioxo-1-piperazinylcarbonylamino)-phenylacetamido]penicillanate | 1 g potency |
| Sterilized Oxacillin sodium | 500 mg potency |

The above ingredients were dissolved in 20 ml of physiological saline solution to obtain an injectable solution.

EXAMPLE 10

| | |
|---|---|
| Sterilized sodium 6-[D(-)-α-(4-ethyl-2, 3-dioxo-1-piperazinylcarbonylamino)-phenylacetamido]penicillanate | 1 g potency |
| Sterilized Cefoxitin sodium | 500 mg potency |

The above ingredients were dissolved in 20 ml of physiological saline solution to obtain an injectable solution.

EXAMPLE 11

| | |
|---|---|
| Sterilized sodium 6-[D(-)-α-(4-ethyl-2, 3-dioxo-1-piperazinylcarbonylamino)-phenylacetamido]penicillanate | 1 g potency |
| Sterilized Flucloxacillin Sodium | 500 mg potency |

The above ingredients were dissolved in 20 ml of physiological saline solution to obtain an injectable solution.

What is claimed is:
1. An antibacterial composition for administration to a host animal, comprising: as active ingredients 6-[D(—)-α-(4-ethyl-2,3-dioxo-1-piperazinylcar- bonylamino)phenylacetamido]-penicillanic acid represented by the formula:

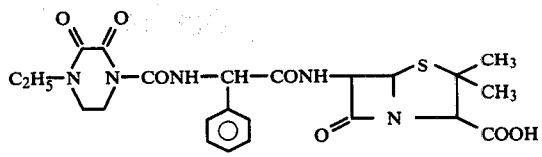

or a pharmaceutically acceptable salt thereof and a β-lactamase-inhibiting penicillin selected from the group consisting of Cloxacillin, Dicloxacillin, Oxacillin, Methicillin, Flucloxacillin and a pharmaceutically acceptable salt thereof, said β-lactamase-inhibiting penicillin being mixed with said penicillanic acid in a ratio of 0.5 to 1.5.

2. The antibacterial composition of claim 1, wherein the pharmaceutically acceptable salt of Cloxacillin, Dicloxacillin, Oxacillin, Methicillin or Flucloxacillin is the sodium salt.

3. The antibacterial composition of claim 1, wherein the pharmaceutically acceptable salt of 6-[D(−)-α-(4-ethyl-2,3-dioxo-1-piperazinylcarbonylamino)-phenylacetamide]penicillanic acid is the sodium salt.

4. The antibacterial composition of claim 3, wherein the β-lactamase-inhibiting penicillin is Cloxacillin sodium.

5. The antibacterial composition of claim 3, wherein the β-lactamase-inhibiting penicillin is Methicillin sodium.

6. An antibacterial composition for administration to a host animal, which comprises: the composition of claim 1 in an injectable form.

7. An antibacterial composition for administration to a host animal, comprising: the composition of claim 1 in a pharmaceutically effective amount in a diluent conventionally used in injections.

* * * * *